United States Patent [19]

Honeycutt

[11] Patent Number: 5,207,837
[45] Date of Patent: May 4, 1993

[54] METHOD OF DISPOSAL OF HOT WATER SOLUBLE GARMENTS AND LIKE FABRICS

[76] Inventor: Travis W. Honeycutt, 3544 Mill Rd., Gainesville, Ga. 30504

[21] Appl. No.: 881,685

[22] Filed: May 12, 1992

Related U.S. Application Data

[63] Continuation-in-part of Ser. No. 683,290, Apr. 10, 1991, abandoned.

[51] Int. Cl.$^5$ .............. B08B 7/00; D03D 1/00; D04B 1/00; D04H 1/00
[52] U.S. Cl. ........................... 134/42; 252/90; 428/224
[58] Field of Search ............... 134/42; 252/90; 428/224

[56] References Cited

U.S. PATENT DOCUMENTS

| | | | |
|---|---|---|---|
| 3,314,809 | 4/1967 | Klug | 106/197.1 |
| 3,413,229 | 11/1968 | Bianco | 252/90 |
| 3,859,125 | 1/1975 | Miller et al. | 428/511 |
| 3,865,918 | 2/1975 | Mitchell et al. | 264/188 |
| 4,343,133 | 8/1982 | Daniels et al. | 53/431 |

*Primary Examiner*—Theodore Morris
*Assistant Examiner*—Zeinab El-Arini
*Attorney, Agent, or Firm*—Malcolm B. Wittenberg

[57] ABSTRACT

A method of disposing of garments after use. The garments, linens, drapes, towels and other useful articles are provided as woven, non-woven, knitted or otherwise formed fabric of thermoplastic polyvinyl alcohol polymer fiber, the fiber being water soluble only at temperatures above approximately 37° C. and preferably above 50° C. After use, the fabric is subjected to water at a sufficient temperature to substantially dissolve the fabric whereupon the water and dissolved fabric are subjected to disposal.

28 Claims, No Drawings

METHOD OF DISPOSAL OF HOT WATER SOLUBLE GARMENTS AND LIKE FABRICS

RELATED APPLICATIONS

The present application is a continuation-in-part of U.S. application Ser. No. 683,290 filed Apr. 10, 1991, now abandoned.

TECHNICAL FIELD OF THE INVENTION

The present invention involves a method of disposing of garments after use. Specifically, the garments are composed of non-woven, woven, knitted or otherwise formed fabric of thermoplastic polymer or fiber which are water soluble at temperatures only above approximately normal human body temperature (37° C).

BACKGROUND OF THE INVENTION

Hospital patient care generates considerable quantities of infectious medical waste in primary and acute care facilities. There has been a general conversion from reusable, cleanable items, to disposable items over the last three decades. These conversions were made to promote antiseptic techniques in patient care and to decrease the potential for cross-infections between patients, staff and the general public. Recent federal and state government regulations such as the Medical Waste Tracking Act of 1988 and OSHA Medical Facility rules have resulted in a substantial increase in medical waste that must be classified as "infectious."

When a patient is admitted to a hospital, the patient produces approximately 55 pounds of medical waste per day. Approximately 20% of this waste is infectious. The current stated objective of the American Hospital Association and the Centers for Disease Control is to treat medical waste as soon as it is generated. Both organizations recognize that medical waste is primarily an occupational hazard for health care workers and not an environmental problem. The best way to deal with infectious medical waste is to disinfect it at the point of generation and dispose of the treated medical waste with minimum handling and storage on premises.

The need for an effective way to dispose of medical waste has been highlighted by the amendment made by to 29 C.F.R. §1910.1030 which provides for the federal regulation under the Occupational Safety And Health Act, 29 U.S.C. 655, 657 to control bloodborne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste in the form of soiled garments and apparel would greatly facilitate compliance with the above-referenced Act.

As a result, consumption of medical disposable woven or non-woven products has been growing at a rate of approximately 10% a year. In 1988, sales totaled approximately 1.155 Billion Dollars. It is projected that by 1992, sales of medical disposable non-woven products will reach 1.54 Billion Dollars.

Disposable medical fabrics are generally currently composed of thermoplastic fibers such as polyethylene, polypropylene, polyesters, polyamides and acrylics. These fabrics can also include mixtures of thermoset fibers such as polyimides, polyarimids and cellulosics. They are typically 10-100 grams per square yard in weight and can be woven, knitted or otherwise formed by methods well known to those in the textile arts while the non-wovens can be thermobonded, hydroentangled, wet laid or needle punched again by methods which are also well known in the textile arts.

Although there is clearly a benefit in the use of disposables in the medical arts by avoiding the necessity of human contact with medical waste which is necessary in the cleaning of comparable reusables, non-biodegradable disposables are posing a problem which is only now being recognized. Landfill sites are becoming increasingly burdened with disposables which do not biodegrade for hundreds of years, if ever. As landfill sites become fully exploited, new sites must be found which are rightfully opposed by residents located proximate to proposed site locations.

It is thus an object of the present invention to provide a method of disposing of garments, linens, drapes, towels and other useful articles after use while avoiding additional burdens being placed upon landfill disposal sites.

It is yet a further object of the present invention to provide a method of disposing of garments, linens, drapes, towels and other useful articles after use such that the garment can be solubilized and medical waste substantially sterilized in a single operation.

These and further objects will be more readily appreciated while considering the following disclosure and appended claims.

SUMMARY OF THE INVENTION

The present invention involves a method of disposing of garments after use which comprises providing the garments as sheets or as woven, non-woven, knitted or otherwise formed fabric of thermoplastic polymer or fiber. The polymer or fabric garments are water soluble only at temperatures above approximately the normal body temperature (37° C.). The garments, linens, drapes, towels and other useful articles composed of said polymer are subjected to water at a sufficient temperature to substantially dissolve the garments whereupon the water and dissolved polymer are subjected to disposal.

DETAILED DESCRIPTION OF THE INVENTION

The present invention deals with the disposal of polymer or fabric configured into such garments and articles as drapes, towels, covers, overwraps, gowns, head coverings, face masks, shoe coverings, CSR wraps, sponges, dressings, tapes, underpads, diapers, wash cloths, sheets, pillow covers, napkins and woven, non-woven, or otherwise formed fabric. Such products are generally employed in the medical industry both in hospitals, outpatient facilities and home environments.

Many of these products generally come into contact with human bodily fluids and their disposal and disinfection has become a matter of major concern in light of the lack of biodegradability of prior products and the potential spread of human fluid-born diseases such as hepatitis B and AIDS.

In order to cope with these difficulties, it is proposed that polymer or fabric employed in the manufacture of such items be composed of polymer fibers which are soluble in hot aqueous baths, including water, either alone or with the addition of surfactants, salts and bleaches above 37° C. and preferably above 50° C. Such fibers or sheets would be insoluble in cold to warm baths below 37° C., the average temperature of the human body. Ideally, the polymer or fabric would be soluble in baths only above 50° C., and, most preferably the polymer or fabric garments would be soluble only in aqueous media between 80° C. to 90° C.

Garments which are soluble in aqueous media below 37° C. are useless as inadvertent secretion of bodily fluids such as blood and urine would cause the polymer to solubilize. Working with polymer which dissolves only at higher temperatures such as above 50° C. or, ideally between 80° C. and 90° C. would prevent inadvertent solubilization yet remain ideal in practicing the present invention. It is contemplated that disposal in a hot water bath such as a washing machine at or near the boiling point of water dedicated solely to solubilizing garments, linens, drapes, towels and other useful articles produced herein would also be an effective disinfecting media. As such, two objectives would be accomplished, namely, that the polymer or sheets would be disinfected and would be solubilized for disposal through the sewer system. Not only would this lessen the burden now being imposed upon current landfill sites but liquid sewer disposal would prove a comparative low cost technique in ridding the user of such used garments.

Polymer or sheet materials useful in practicing the present method comprise polyvinyl alcohol with or without acetyl groups, cross-linked or uncross-linked. Ideally, the garments are comprised of polyvinyl alcohol homopolymer that has been highly crystallized by post drawing or heat annealing. Ideal for use in the present invention would be a highly crystallized totally saponified polyvinyl acetate. Commercially, polyvinyl alcohol sold under the trademark Vinex 1003 ™ by Air Products could be used herein. Useful fibers are typically 0.5 denier to 5.0 denier and are preferably from 1.0–2.0 denier and most preferably sized at 1.2–1.5 denier. A commercially available product for use in the present invention is either type T-B (VEE 1290) or type T-5 (VpB 101) which are each available from Kuralon as its PVA fiber. This material is sold in 44 mm lengths. The T-B product is sized at 1.2 denier while the T-5 product is sold in 38 mm staple lengths of 1.5 denier.

The fabric useful in practicing the present invention can be constructed by any well known technique for making woven, non-woven, knitted or otherwise formed fabric. Such non-woven techniques useful in practicing the present invention include spin bonding, melt blowing or wet laying, hydroentangling with cold water and/or thermally bonding with 30–70% of the surface melted to form, for example, a diamond pattern. When products, such as diapers, are configured of sheets of suitable thermoplastic material, the sheets are approximately 1 to 6 mils in thickness and more preferably 1 to 3 mils in thickness and most preferably approximately 1.5 mils in thickness. Suitable non-woven fabric or sheets are approximately from 15 g/yd² to 200 g/yd² in weight and more preferably from 20 g/yd² to 70 g/² and most preferably from 25 g/yd² to 80 g/yd². Knitted or woven fabrics are approximately 50% heavier as needed for binding tapes, cuffs and related appendages.

As examples the following fabric samples were manufactured on conventional thermal bonding equipment.

| I.D. | TL-0079.0 | 79.1 | 79.2 | 080.0 | 0080.1 |
|---|---|---|---|---|---|
| Fibre | Kuralon T-5 PVA (1.5 denier, 38 mm staple length) | | | | |
| Pattern No. | 2 | 2 | 2 | 1 | 1 |

| I.D. | TL-0079.0 | 79.1 | 79.2 | 080.0 | 0080.1 |
|---|---|---|---|---|---|
| Fabric Wt. (gms/sq. yd) | 27 | 44 | 47 | 35 | 43 |
| Thickness (mil) | 15 | 12 | 17 | 14 | 16 |
| Tensiles- (Grab-lbs) | | | | | |
| Dry MD | 8.3 | 11.7 | 16.6 | 13.8 | 16.1 |
| Wet MD | 3.2 | 4.8 | 4.6 | 3.1 | 6.0 |
| Dry CD | 2.0 | 2.3 | 4.3 | 3.8 | 5.2 |
| Wet CD | 1.0 | 1.5 | 1.7 | 1.3 | 2.3 |
| Elongation (%) | | | | | |
| Dry MD | 11 | 10 | 12 | 12 | 11 |
| Dry CD | 48 | 30 | 38 | 19 | 22 |
| Mullen Burst (psi) | | | | | |
| Dry | 11 | 15 | 19 | 13 | 16 |
| Wet | 10 | 14 | 19 | 13 | 15 |
| Hanle-O-Meter (gms) | 84 | 244 | 432 | 173 | 244 |
| Trap Tear-MD | 1.7 | 2.1 | 3.5 | 2.7 | 2.9 |
| CD | 0.4 | 0.4 | 0.8 | 0.6 | 0.7 |

It was found that the above-manufactured fabric displayed nearly identical physical properties similar to fabric manufactured from polyester and polyproplyene. However, the fabric manufactured above was unaffected by cool or warm water (23°–37° C.) but when exposed to hot water (80°–90° C.), immediately dissolved.

There have been prior uses of polyvinyl alcohol which rely upon the polymer's solubility characteristics. For example, U.S. Pat. No. 3,413,229 teaches a water soluble packing for insecticides, medicines, chemicals, dyes, pigments, industrial additives and similar materials. In effect, the patent applies no criticality to the media for dissolving its PVA pouch and, in this regard, it teaches away from the practice of the present method. Furthermore, there is absolutely no disclosure of producing garments, linens, drapes, towels and other useful articles from PVA polymer.

U.S. Pat. No. 3,859,125 teaches producing paper coated with a solution of polyvinyl alcohol to produce a wide variety of useful products. Because the paper is coated with amorphous polyvinyl alcohol, there are no controls placed upon the composite product to dissolve the polyvinyl alcohol component only at certain critical temperatures. In addition, if one were to coat a paper support as taught in the '125 patent and then crystalize the polyvinyl alcohol coating by postdrawing, for example, the paper support would undoubtedly tear, rendering the final product useless.

Conceivably, one could practice the present invention while employing a paper support but, in doing so, a crystallized fully formed layer of polyvinyl alcohol would be required in order to achieve the minimum solubility temperature requirements asserted herein. The bonding of a paper support with a crystallized form of polyvinyl alcohol is not taught in the '125 patent and, as a result, there is no discussion of critical solubility temperatures.

The ideal product produced pursuant to the present invention is a fabric created from crystallized polyvinyl alcohol as a stand alone film. A stand alone film is much stronger than a coated composite. The paper component of the '125 patent must be so thin and flimsy that the garment will, in all likelihood lack the structural integrity necessary for a commercial product. In addition, stand alone film is completely water soluble while paper does not solubilize in water. At best, paper is water dispersible.

What is claimed is:

1. A method of disposing of thermoplastic polymer fabric of polyvinyl alcohol fiber after use, said fabric being configured into one or more members selected from the group consisting of drapes, towels, covers, overwraps, gowns, head covers, face masks, shoe coverings, sponges, dressings, tapes, underpads, diapers, wash cloths, sheets, pillow covers and napkins, said polyvinyl alcohol fiber being water soluble only at temperatures above 37° C. and insoluble at temperatures below 37° C. and subjecting said thermoplastic polymer fabric after use to an aqueous bath to dissolve said polymer fabric whereupon said dissolved polymer fabric is subjected to disposal, said polymer fabric comprising a polyvinyl alcohol homopolymer that has been highly crystallized by post drawing or by heat annealing.

2. The method of claim 1 wherein said fabric is woven, non-woven or knitted of said thermoplastic polymer.

3. The method of claim 1 wherein said thermoplastic polymer fabric is water soluble only at temperatures above 50° C. and insoluble at temperatures below 50° C.

4. The method of claim 1 wherein said thermoplastic polymer fabric is water soluble only at temperatures between 80° C.–90° C.

5. The method of claim 1 wherein said fabric is a non-woven thermoplastic polymer of polyvinyl alcohol having a weight of approximately 25–80 g/yd$^2$.

6. The method of claim 1 wherein said fiber is approximately 0.5–5.0 denier in size.

7. The method of claim 1 wherein said fiber is approximately 1.0–2.0 denier in size.

8. The method of claim 1 wherein said fiber is from approximately 1.2–1.5 denier in size.

9. The method of claim 1 wherein said fabric is prepared from said fiber by spun bonding.

10. The method of claim 1 wherein said fabric is prepared from said fiber by melt blowing.

11. The method of claim 1 wherein said fabric is prepared by wet laying and hydroentangling said fiber.

12. The method of claim 1 wherein said fabric is prepared thermally bonding said fiber.

13. The method of claim 12 wherein said fiber is thermally bonded after hydroentanglement.

14. The method of claim 1 wherein approximately 30–70% of the fabric surface is melted by thermal bonding.

15. A method of disposing thermoplastic polymer fabric of polyvinyl alcohol fiber after use, said fabric being configured into one or more members selected from the group consisting of drapes, towels, covers, overwraps, gowns, head covers, face masks, shoe coverings, CSR wraps, sponges, dressings, tapes, underpads, diapers, wash cloths, sheets, pillow covers and napkins, said polyvinyl alcohol fiber being water soluble only at temperatures above 37° C. and insoluble at temperatures below 37° C. and subjecting said thermoplastic polymer fabric after use to an aqueous bath to dissolve said polymer fabric whereupon said dissolved polymer fabric is subjected to disposal, said polymer fabric comprising polyvinyl alcohol that has been produced from crystallized substantially totally saponified polyvinyl acetate.

16. The method of claim 15 wherein said fabric is woven, non-woven or knitted of said thermoplastic polymer.

17. The method of claim 15 wherein said thermoplastic polymer fabric is water soluble only at temperatures above 50° C. and insoluble at temperatures below 50° C.

18. The method of claim 15 wherein said thermoplastic polymer fabric is water soluble only at temperatures between 80° C. and 90° C.

19. The method of claim 15 wherein said fabric is a non-woven thermoplastic polymer of polyvinyl alcohol having a weight of approximately 25–80 g/yd$^2$.

20. The method of claim 15 wherein said fiber is approximately 0.5–5.0 denier in size.

21. The method of claim 15 wherein said fiber is approximately 1.0–2.0 denier in size.

22. The method of claim 15 wherein said fiber is from approximately 1.2–1.5 denier in size.

23. The method of claim 15 wherein said fabric is prepared from said fiber by spun bonding.

24. The method of claim 15 wherein said fabric is prepared from said fiber by melt blowing.

25. The method of claim 15 wherein said fabric is prepared by wet laying and hydroentangling said fiber.

26. The method of claim 15 wherein said fabric is prepared by thermally bonding said fiber.

27. The method of claim 26 wherein said fiber is thermally bonded after hyroentanglement.

28. The method of claim 15 wherein approximately 30–70% of the fabric surface is melted by thermal bonding.

* * * * *

REEXAMINATION CERTIFICATE (2912th)
United States Patent [19]
Honeycutt

[11] B1 5,207,837
[45] Certificate Issued  *Jun. 11, 1996

[54] METHOD OF DISPOSAL OF HOT WATER SOLUBLE GARMENTS AND LIKE FABRICS

[75] Inventor: Travis W. Honeycutt, Gainsville, Ga.

[73] Assignee: Isoyser Comp., Inc., Norcross, Ga.

[ * ] Notice: The term of this patent shall not extend beyond the expiration date of Pat. No. 5,181,966.

Reexamination Request:
No. 90/003,802, Apr. 24, 1995

Reexamination Certificate for:
Patent No.: 5,207,837
Issued: May 4, 1993
Appl. No.: 881,685
Filed: May 12, 1992

Related U.S. Application Data

[63] Continuation-in-part of Ser. No. 683,290, Apr. 10, 1991, abandoned.

[51] Int. Cl.⁶ ............... B08B 7/00; D03D 1/00; D04B 1/00; D04H 1/00
[52] U.S. Cl. ............... 134/42; 252/90; 428/224
[58] Field of Search ............ 134/42; 252/90; 428/224

[56] References Cited

U.S. PATENT DOCUMENTS

| | | | |
|---|---|---|---|
| 3,484,874 | 12/1969 | Bickenheuser, Jr. | 4/112 |
| 3,762,454 | 10/1973 | Wilkins, Jr. | 150/1 |
| 3,886,610 | 6/1975 | Shelden | 5/81 R |
| 5,051,222 | 9/1991 | Marten et al. | 264/143 |
| 5,181,966 | 1/1993 | Honeycutt et al. | 134/42 |
| 5,181,967 | 1/1993 | Honeycutt | 134/42 |

FOREIGN PATENT DOCUMENTS

| | | |
|---|---|---|
| 8902229 | 1/1990 | Brazil . |
| 0050288 | 10/1981 | European Pat. Off. . |
| 0107576 | 5/1984 | European Pat. Off. . |
| 0176316 | 4/1986 | European Pat. Off. . |
| 0272816 | 6/1988 | European Pat. Off. . |
| 1519530 | 4/1970 | Germany . |
| 3017246 | 11/1981 | Germany . |
| 47-41741 | 10/1972 | Japan . |
| 55-71532 | 5/1980 | Japan . |
| 59-100704 | 6/1984 | Japan . |
| 60-44897 | 3/1985 | Japan . |
| 61-159995 | 7/1986 | Japan . |
| 2-68396 | 3/1990 | Japan . |
| 386161 | 1/1933 | United Kingdom . |
| 743165 | 1/1956 | United Kingdom . |
| 1187690 | 4/1970 | United Kingdom . |
| 1374199 | 11/1974 | United Kingdom . |
| 1451619 | 10/1976 | United Kingdom . |
| 2102461 | 2/1983 | United Kingdom . |
| 2119709 | 11/1983 | United Kingdom . |
| 2211196 | 6/1989 | United Kingdom . |
| 2211088 | 6/1989 | United Kingdom . |
| 2248842 | 4/1992 | United Kingdom . |
| WO91/14413 | 10/1991 | WIPO . |
| WO91/17210 | 11/1991 | WIPO . |

OTHER PUBLICATIONS

Hopper et al., Essentials of English, 4th ed., p. 223 (1990).

J. Brandrup et al., Polymer Handbook, 3rd ed., p. 435 (1989).

Plastics Compounding, 1993/1994, p. 41.

*Encyclopedia of Polymer Science and Engineering*, vol. 17, p. 192, John Wiley & Sons, Inc., New York (1989).

*Primary Examiner*—Zeinab El-Arini

[57] ABSTRACT

A method of disposing of garments after use. The garments, linens, drapes, towels and other useful articles are provided as woven, non-woven, knitted or otherwise formed fabric of thermoplastic polyvinyl alcohol polymer fiber, the fiber being water soluble only at temperatures above approximately 37° C. and preferably above 50° C. After use, the fabric is subjected to water at a sufficient temperature to substantially dissolve the fabric whereupon the water and dissolved fabric are subjected to disposal.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15–28 are confirmed.

Claim 1 is determined to be patentable as amended.

Claims 2–14, dependent on an amended claim, are determined to be patentable.

New claims 29–34 are added and determined to be patentable.

1. A method of disposing of thermoplastic polymer fabric of polyvinyl alcohol fiber after use, said fabric being configured into one or more members selected from the group consisting of drapes, towels, covers, overwraps, gowns, head covers, face masks, shoe coverings, sponges, dressings, tapes, underpads, diapers, wash cloths, sheets, pillow covers and napkins, said polyvinyl alcohol fiber being water soluble only at temperatures above 37° C. and insoluble at temperatures below 37° C. and subjecting said thermoplastic polymer fabric after use to an aqueous bath to dissolve said polymer fabric whereupon said dissolved polymer fabric is subjected to disposal, said polymer fabric comprising a polyvinyl alcohol homopolymer that has been [highly] crystallized by postdrawing or by heat annealing.

*29. The method of claim 1, wherein the polyvinyl alcohol homopolymer has been crystallized by post-drawing.*

*30. The method of claim 1, wherein the polyvinyl alcohol homopolymer has been crystallized by heat annealing.*

*31. The method of claim 1, wherein the crystallized polyvinyl alcohol is produced from substantially totally saponified polyvinyl acetate.*

*32. The method of claim 15, wherein the polyvinyl alcohol has been crystallized by post-drawing.*

*33. The method of claim 15, wherein the polyvinyl alcohol has been crystallized by heat annealing.*

*34. The method of claim 15, wherein the polyvinyl alcohol has been crystallized by post-drawing or heat annealing.*

* * * * *